United States Patent [19]

Erpenbach et al.

[11] 4,280,009
[45] Jul. 21, 1981

[54] CONTINUOUS PRODUCTION OF 2-ETHYL-HEXYL ACRYLATE FREE FROM DIOCTYLETHER

[76] Inventors: Heinz Erpenbach; Klaus Guhrmann; Herbert Joest, all c/o Hoechst Aktiengesellschaft, Werk Knapsack, Knapsack bei Cologne, Fed. Rep. of Germany

[21] Appl. No.: 66,510

[22] Filed: Aug. 14, 1979

Related U.S. Application Data

[63] Continuation of Ser. No. 797,812, Oct. 26, 1976, abandoned.

[30] Foreign Application Priority Data

Oct. 30, 1975 [DE] Fed. Rep. of Germany ....... 2548561

[51] Int. Cl.$^2$ .............................................. C07C 9/54
[52] U.S. Cl. ..................................................... 560/205
[58] Field of Search ......................................... 560/205

[56] References Cited

U.S. PATENT DOCUMENTS

| | | | |
|---|---|---|---|
| 3,458,561 | 7/1969 | Kautter | 560/205 |
| 3,875,512 | 4/1975 | Ohrui et al. | 560/205 |
| 3,882,167 | 5/1975 | Lohmor et al. | 560/205 |
| 3,894,076 | 7/1975 | Van Duyne et al. | 560/205 |

FOREIGN PATENT DOCUMENTS

| | | | |
|---|---|---|---|
| 45-33049 | 10/1970 | Japan | 560/205 |
| 1387704 | 3/1975 | United Kingdom | 560/206 |

*Primary Examiner*—Paul J. Killos

[57] ABSTRACT

2-ethyl-hexylacrylate free from dioctylether is produced continuously by reacting acrylic acid and 2-ethyl-hexanol-(1) in a molar ratio of 1:1 to 1:2 at 85° to 140° C. in the presence of an acid catalyst. More specifically, acrylic acid, 2-ethyl-hexanol-(1) and a sulfuric acid catalyst are continuously introduced into a reaction zone; resulting reaction water is distilled off azeotropically together with 2-ethyl-hexanol-(1) near the head of a first distilling zone being mounted on the reaction zone; the azeotrope is condensed and separated into an alcoholic phase and an aqueous phase; the alcoholic phase is recycled to the head of the first distilling zone and the aqueous phase is removed; reaction mixture maintained for a period of 2 to 8 hours in the reaction zone is conveyed from the reaction zone to a second distilling zone; 2-ethyl-hexanol-(1) in excess is distilled off overhead together with traces of unreacted acrylic acid and the distillate is recycled to the reaction zone; base product obtained in the second distilling zone is delivered to a third distilling zone; pure 2-ethyl-hexylacrylate is distilled off overhead and high-boiling residue is removed from the base of the third distilling zone.

3 Claims, 1 Drawing Figure

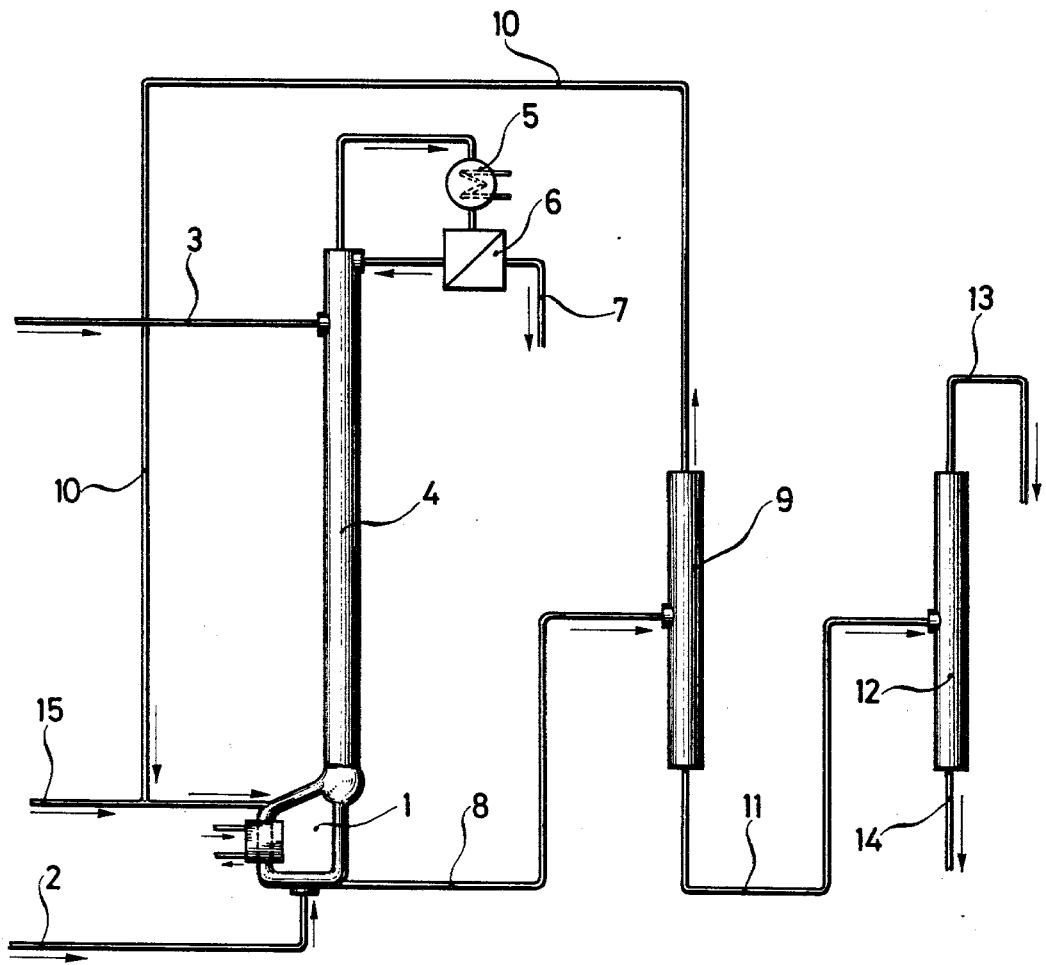

CONTINUOUS PRODUCTION OF 2-ETHYL-HEXYL ACRYLATE FREE FROM DIOCTYLETHER

This application is a continuation of application Ser. No. 797,812 filed Oct. 26, 1976 now abandoned.

The preparation of 2-ethyl-hexylacrylate (acrylic acid-(2-ethylhexyl)-ester; $CH_2=CH-C(O)OCH_2-CH(C_2H_5)-(CH_2)_3-CH_3$) by reacting acrylic acid with 2-ethylhexanol-(1) in liquid phase at elevated temperature and in the presence of a sulfonic acid catalyst has already been described, e.g. in U.S. Pat. No. 2,917,538. This reaction is an equilibrium reaction, wherein the rate of conversion of the acid or alcohol to the ester is critically determined by the equilibrium constant. In view of this, it has been suggested that the rate of conversion of acrylic acid to the ester be increased by using 2-ethyl-hexanol-(1) in a molar excess over acrylic acid and removing the reaction water by azeotropic distillation with an entrainer. In these processes it is, however, necessary for the entrainer to be separated, and for the unreacted acrylic acid contained in the ester to be neutralized, which is disadvantageous. Next, it is necessary in a technically expensive operation to separate the neutralization products and to recover the acrylic acid by acidification with hydrochloric acid with the resultant formation of a salt whereby wastewater preparation is rendered difficult.

Further processes for making 2-ethyl-hexylacrylate, wherein lower acrylic acid esters are subjected to an ester interchange reaction with 2-ethyl-hexanol-(1) have been described in German Patent Specification No. 1,067,805 and U.K. Patent Specification No. 960,005. Disadvantages which are encountered with these prior processes reside in the fact that it is necessary for the excess acrylic acid ester to be circulated and in the fact that lower alcohol by-products (methanol, ethanol) are obtained in stoichiometric quantities.

It is an object of the present invention to avoid the disadvantageous phenomena described hereinabove and provide a process for the continuous production of 2-ethyl-hexylacrylate free from dioctylether by reacting acrylic acid and 2-ethyl-hexanol-(1) in a molar ratio of 1:1 to 1:2 at temperatures of 85° to 140° C. in the presence of an acid catalyst and distillatively purifying the resulting ester, which process comprises: continuously introducing acrylic acid, 2-ethyl-hexanol-(1) and a sulfuric acid catalyst into a reaction zone; distilling off the resulting reaction water azeotropically together with the 2-ethyl-hexanol-(1) near the head of a first distilling zone being mounted on the reaction zone; condensing the azeotrope and separating it into an alcoholic phase and an aqueous phase; recycling the alcoholic phase to the head of the first distilling zone and removing the aqueous phase; conveying reaction mixture maintained for a period of 2 to 8 hours in the reaction zone from the reaction zone to a second distilling zone; distilling off overhead 2-ethyl-hexanol-(1) in excess together with traces of unreacted acrylic acid and recycling the distillate to the reaction zone; delivering base product obtained in the second distilling zone to a third distilling zone; distilling overhead pure 2-ethyl-hexylacrylate and removing a high-boiling residue from the base of the third distilling zone.

Further preferred features of the present process provide:

(a) for a concentration of 0.2 to 1.5 weight % of sulfuric acid to be maintained in the reaction mixture in the reaction zone, and (b) for the 2-ethyl-hexanol-(1) to be introduced into the reaction zone through the first distilling zone mounted on the reaction zone.

The esterification reaction may preferably be effected at temperatures of 95° to 125° C. Temperatures higher than specified herein favor the formation of dioctylether and polymerization, whereas temperatures lower than specified herein considerably affect the reaction velocity. The concentration of the sulfuric acid in the reaction mixture under circulation should preferably not exceed 5 weight % in order not to favor the dehydration of 2-ethyl-hexanol-(1).

The esterification reaction and distillative separation are preferably effected in the presence of 0.01 to 0.1 weight % of a suitable polymerization inhibitor, which may be selected, for example, from hydroquinone, hydroquinone monomethylether, p-benzoquinone, phenothiazine or methylene blue, and used in combination with air, if desired or convenient.

A preferred version of the present process will now be described with reference to the accompanying flow scheme.

Reaction mixture kept circulating in a reactor (1) is continuously admixed with acrylic acid through a conduit (2). 2-ethyl-hexanol-(1) is introduced via a conduit (3) into the upper third of a distilling column (4) mounted on the reactor (1). The mixture kept circulating in the reactor (1) is maintained at a reaction temperature of 95° to 125° C. under a pressure of 50 to 200 mm Hg. Near the head of the distilling column (4), there is distilled off at 25° to 75° C. under a pressure of 50 to 200 mm Hg an azeotrope comprising the reaction water and 2-ethyl-hexanol-(1), which is condensed in a condenser (5) and separated into two phases in a separator (6). The aqueous phase is removed through a conduit (7) and the alcoholic phase is recycled to the head of the distilling column (4). The esterification mixture is taken from the reactor (1) through a conduit (8) and introduced into a second distilling column (9). In the column (9), there are distilled off under a pressure of 20 to 150 mm Hg and at a head temperature of 70° to 150° C. 2-ethyl-hexanol-(1) in excess and traces of acrylic acid, at a reflux ratio of 1 to 5 and recycled to the reactor (1) through a conduit (10). Crude ester is removed from the base of the column (9) at 100° to 180° C. and delivered to a third distilling column (12) through a conduit (11). Pure ester free from dioctylether is distilled off near the head of distilling column (12) under a pressure of 10 to 100 mm Hg, at 90° to 150° C. and a reflux ratio of 0.1–2, and removed through a conduit (13). High boiling residues accumulate in the base of the column (12) at 100° to 180° C. They are removed through a conduit (14).

The concentration of sulfuric acid in the reaction mixture in the reactor (1) is kept constant by supplying the reactor (1) with fresh sulfuric acid through a conduit (15).

EXAMPLE

The reactor (1) was a stainless steel circulation reactor. The capacity was 18 l of liquid matter containing 1 weight % of a sulfuric acid catalyst, under the operational conditions selected. One side of the reactor was jacketed and heated by means of steam. The reaction temperature was 119° C. and the pressure was 100 mm Hg. The reactor was fed with 1080 g/h (15 mol) of fresh acrylic acid (through the conduit (2)) and with 2015 g/h (15.5 mol) of fresh 2-ethyl-hexanol-(1) (through the conduit (3)). The 2-ethyl-hexanol-(1) was recycled through the conduit (10), and 39 g/h of sulfuric acid was introduced into the reactor (1) through the conduit (15). In other words, reactor (1) was fed with altogether 3894 g/h of a mixture composed of 1080 g/h (15 mol) of acrylic acid, 2775 g/h (21.35 mol) of 2-ethyl-hexanol-(1) and 39 g/h of sulfuric acid. The acrylic acid and 2-ethyl-hexanol-(1) were accordingly used in a molar ratio of 1:1.42. After a residence time of 4 hours in the reactor, the acrylic acid was found to have been transformed quantitatively. 338 g/h of water/ethyl hexanolazeotrope was distilled off near the head of the first distilling column (4) mounted on the reactor. The distilling column was operated under a pressure of 100 mm Hg and at 35° C. The azeotrope was separated into two phases in the separator (6). The organic phase was recycled to the column (4) and 270 g/h of an aqueous phase was removed through the conduit (7). 3624 g/h of reaction mixture was taken from the reactor (1) through the conduit (8) and delivered to the second distilling column (9), which was operated under a pressure of 100 mm Hg, at a head temperature of 122° C. and at a reflux ratio of 3, and in which altogether 760 g of ethylhexanol was distilled off and recycled to the reactor through the conduit (10). 2864 g of crude ester was taken at 165° C. from the base of the column (9) and delivered to the third distilling column (12). The column (12) was operated at a head temperature of 130° C., under a pressure of 50 mm Hg and at a reflux ratio of 0.5. 2650 g (14.4 mol) of 2-ethyl-hexyl acrylate with a purity of 99.98% by weight was obtained as the head product which was free from dioctylether. The yield was 96%, based on the acrylic acid which underwent conversion, or 93.6%, based on the ethyl hexanol which underwent conversion. 214 g of high-boiling material was removed from the base of column (12) at 170° C.

The esterification mixture, distillate and reflux material contained 0.05 weight % of a stabilizer, which was a mixture of phenothiazine and hydroquinone.

We claim:

1. An improved process for the continuous production of 2-ethyl-hexlacrylate free from dioctylether by reacting acrylic acid and 2-ethyl-hexanol-(1) in a molar ratio of 1:1 to 1:2 at temperatures of 85° to 140° C. in the presence of an acid catalyst the improvement which is: continuously introducing essentially only acrylic acid, 2-ethyl-hexanol-(1) and a sulfuric acid catalyst into a reaction zone; distilling off the resulting reaction water azeotropically together with the 2-ethyl-hexanol-(1) near the head of a first distilling zone being mounted on the reaction zone; condensing the azeotrope and separating it into an alcoholic phase and an aqueous phase; recycling the alcoholic phase to the head of the first distilling zone and removing the aqueous phase; conveying reaction mixture maintained for a period of 2 to 8 hours in the reaction zone from the reaction zone to a second distilling zone; distilling off overhead 2-ethyl-hexanol-(1) in excess together with traces of unreacted acrylic acid and recycling the distillate to the reaction zone; delivering base product obtained in the second distilling zone to a third distilling zone; distilling overhead pure 2-ethyl-hexylacrylate and removing a high-boiling residue from the base of the third distilling zone.

2. A process as claimed in claim 1, wherein a concentration of 0.2 to 1.5 weight % of sulfuric acid is maintained in the reaction mixture in the reaction zone.

3. A process as claimed in claim 1, wherein the 2-ethyl-hexanol-(1) is introduced into the reaction zone through the first distilling zone mounted on the reaction zone.

* * * * *

UNITED STATES PATENT OFFICE
CERTIFICATE OF CORRECTION

Patent No. 4,280,009          Dated July 21, 1981

Inventor(s) Erpenbach et al

It is certified that error appears in the above-identified patent and that said Letters Patent are hereby corrected as shown below:

On the cover page left column, change

"Inventors: Heinz Erpenbach; Klaus Guhrmann; Herbert Joest, all c/o Hoechst Aktiengesellschaft, Werk Knapsack, Knapsack bei Cologne, Fed. Rep. of Germany"

to

--Inventors: Heinz Erpenbach, Sürth bei Köln; Klaus Gehrmann, Erftstadt-Lechenich; Herbert Joest, Erftstadt-Lechenich; all of Fed. Rep. of Germany--

On the cover page left column under the column headed "Inventors:" insert

--Assignee: Hoechst Aktiengesellschaft, Fed. Rep. of Germany--

Signed and Sealed this

Eleventh Day of May 1982

[SEAL]

Attest:

GERALD J MOSSINGHOFF

Attesting Officer      Commissioner of Patents and Trademarks